US010813548B2

(12) United States Patent
van Dijk

(10) Patent No.: US 10,813,548 B2
(45) Date of Patent: Oct. 27, 2020

(54) METHOD, SYSTEM AND COMPUTER READABLE MEDIUM TO DETERMINE A STRABISMUS ANGLE BETWEEN THE EYES OF AN INDIVIDUAL

(71) Applicant: Stichting VUmc, Amsterdam (NL)

(72) Inventor: Bob Wilhelm van Dijk, Amsterdam (NL)

(73) Assignee: Stichting VUmc, Amsterdam (NL)

( * ) Notice: Subject to any disclaimer, the term of this patent is extended or adjusted under 35 U.S.C. 154(b) by 173 days.

(21) Appl. No.: 16/070,042

(22) PCT Filed: Jan. 11, 2017

(86) PCT No.: PCT/NL2017/050011
§ 371 (c)(1),
(2) Date: Jul. 13, 2018

(87) PCT Pub. No.: WO2017/123086
PCT Pub. Date: Jul. 20, 2017

(65) Prior Publication Data
US 2019/0029511 A1 Jan. 31, 2019

(30) Foreign Application Priority Data
Jan. 13, 2016 (NL) ...................... 2016085

(51) Int. Cl.
*A61B 3/08* (2006.01)
*A61B 3/00* (2006.01)
*A61B 3/11* (2006.01)
*A61B 3/113* (2006.01)

(52) U.S. Cl.
CPC ............ *A61B 3/085* (2013.01); *A61B 3/0083* (2013.01); *A61B 3/111* (2013.01); *A61B 3/113* (2013.01)

(58) Field of Classification Search
CPC ....................................................... A61B 3/085
USPC ......................................................... 351/209
See application file for complete search history.

(56) References Cited

U.S. PATENT DOCUMENTS

| 9,041,787 B2 | 5/2015 | Andersson et al. | |
| 2015/0085253 A1* | 3/2015 | Walsh | A61B 3/102 351/208 |

FOREIGN PATENT DOCUMENTS

| GB | 2332271 A | 6/1999 |
| WO | 87/02565 A1 | 5/1987 |
| WO | 2011/021936 A1 | 2/2011 |
| WO | 2014/204904 A1 | 12/2014 |

* cited by examiner

*Primary Examiner* — James C. Jones
(74) *Attorney, Agent, or Firm* — Hoffmann & Baron, LLP

(57) ABSTRACT

A method, system and computer readable medium for determining a strabismus angle of the eyes of an individual by: positioning the individual with his or her eyes in front of an eye tracker device and in front of a screen at a viewing distance; displaying a small image element on the screen; measuring a position and line of sight of the eyes of the individual with the eye tracker device while the individual is focussing on the small image element; forwarding the measured position and line of sight of the eyes from the eye tracker device to a computer system; and, calculating the strabismus angle between the eyes by calculating the difference in line of sight of the left and right eyes of the individual.

25 Claims, 2 Drawing Sheets

METHOD, SYSTEM AND COMPUTER READABLE MEDIUM TO DETERMINE A STRABISMUS ANGLE BETWEEN THE EYES OF AN INDIVIDUAL

CROSS-REFERENCE TO RELATED APPLICATIONS

This application is the National Stage of International Application No. PCT/NL2017/050011, filed Jan. 11, 2017, which claims the benefit of Netherlands Application No. NL 2016085, filed Jan. 13, 2016, the contents of which is incorporated by reference herein.

FIELD OF THE INVENTION

The invention relates a method to determine a strabismus angle between the eyes in a direction of gaze of an individual comprising:
providing an eye tracker device to follow the viewing direction of the eyes of the individual;
positioning the individual in front of a screen at a viewing distance;
having the individual to view on the screen;
measuring a position and line of sight of the eyes of the individual with the eye tracker device; and
forwarding the measured position and line of sight of the eyes from the eye tracker device to a computer system.
The strabismus angle may be determined when the dominant eye gazes in one or all nine cardinal directions, e.g. straight ahead, up, down, left, right, and the left/up, left/down, right/up and right/down diagonal directions with the computer system.

BACKGROUND OF THE INVENTION

About two to five percent of children and adults are affected by strabismus. Strabismus is a failure of the two eyes to maintain proper alignment and work together. When the eyes fixate on an object, one eye—the non-dominant eye—is misaligned. This misalignment can cause visual confusion and double vision. It is important to treat children with strabismus to prevent amblyopia. Which will occur when the brain ignores the visual input from the misaligned eye, to prevent double vision. When treatment with glasses, eye training or patches are insufficient, an eye surgery is necessary. Strabismus surgery involves recession or resection of one eye muscle. For this surgery, the strabismus angle must be determined. Currently the standard to measure may be the prism cover test and the alternate prism cover test. However, these tests have multiple disadvantages. Firstly, they are relatively inaccurate, i.e. between 2° and 5°. Secondly, the duration of the measurements is relatively long. Which is 10-15 minutes to estimate the angle of strabismus at near and distance fixation, to almost 45 minutes for the determination of the angle of strabismus in the nine gaze directions at near and distance fixation. Thirdly, a high level of cooperation is required, which makes the test less applicable, especially when applied to young children.

A new method to determine the strabismus angle is necessary because now 20 to 50 percent of the eye operations are unsuccessful, and a second eye operation is needed. 20% of the reoperations in strabismus surgery may be caused by inaccuracy in the determination of the angle of strabismus. A second operation is, as you can imagine, undesirable. The amount of unsuccessful operations are partly caused due to the very difficult eye mechanism that can lead to a wrong shift or shortening of the eye muscle in operation. Another important factor that plays a role in the high number unsuccessful operations is that this strabismus angle is still determined by hand and therefore, there is a greater chance of incorrect measured strabismus angle.

GB2332271 and WO2011/021936 show automated assessment of strabismus patients.

Dmitri Model and Moshe Eizenman, "an automated Hirschberg test for infants", IEEE transactions on biomedical engineering, Vol 58, No 1, January 2011, discloses an automated test for measuring the eye misalignment in infants. Nine animated images (2 cm×2 cm) were presented sequentially at different positions on a monitor and 450 estimates of the eye alignment were recorded at a rate of 30 estimates per second with an eye tracker to determine the eye misalignment.

SUMMARY OF THE INVENTION

It is an objective to provide an improved or alternative method to determine strabismus angles between the eyes of an individual.

Accordingly there is provided a method to determine a strabismus angle between the eyes in a direction of gaze of an individual comprising:
providing an eye tracker device to follow the viewing direction of the eyes of the individual;
positioning the individual in front of a screen at a viewing distance;
having the individual to view on the screen;
measuring a position and line of sight of the eyes of the individual with the eye tracker device; and
forwarding the measured position and line of sight of the eyes from the eye tracker device to a computer system;
wherein the method comprises:
displaying a small image element at a target position on the screen to have the individual to focus his or her eyes on the small image element on the screen; and
calculating the strabismus angles between the eyes by calculating the difference in the horizontal and vertical gaze directions between the eyes of the individual with a computer system when a dominant eye gazes in the direction of the small image element.

By displaying a small image element at a target position on the screen the individual has to really focus his or her eyes on the screen to see the image and thereby it becomes possible to measure a position and line of sight of the eyes of the individual with the eye tracker device with high precision making a good calculation of the strabismus angle of the eyes possible.

According to a further embodiment displaying a small image element comprises displaying an image element smaller than 20 arc min, preferably smaller than 10 arc min and most preferably smaller than 2 arc min at least at the resolution limit of the eyes of the individual.

By displaying a small image smaller than 20 arc min, preferably smaller than 10 arc min and most preferably smaller than 2 arc min but bigger than the resolution limit of the eyes of the individual at a target position on the screen the individual has to really focus his or her eyes on the screen to see the image and thereby it becomes possible to measure a position and line of sight of the eyes of the individual with the eye tracker device with high precision making a good calculation of the strabismus angle of the eyes possible.

According to a further embodiment the method further comprises:

using the computer system to display the small image element at the target position on the screen;

calculating a viewing position on the screen by using the measured position and line of sight of the eyes with the computer system;

calculating a distance between the target position on the screen and the calculated viewing position on the screen;

if the distance is smaller than 60 arc min calculating the strabismus angle of the eyes by calculating the difference in line of sight of the left and right eyes of the individual with the computer system.

If the distance between the target position on the screen and the calculated viewing position on the screen is smaller than 60 arc min the individual has really focused the eyes on the target assuring a good measurement.

According to a further embodiment displaying a small image element at a position on the screen comprises displaying a small image element at a target position on the screen within a larger background image and measuring the position and line of sight of the eyes of the individual with the eye tracker device while the individual scans the background to find the small image element.

Displaying a small image element at a target position on the screen in a larger background image will draw the attention of the individual to focus his or her eyes on the small image for good results.

According to a further embodiment displaying a small image element at a target position on the screen comprises displaying a small target image element appearing or not appearing at a position on the screen within the background image and measuring the position and line of sight of the eyes of the individual with the eye tracker device while the individual scans the background to find the small image element.

Displaying a small image element appearing at a target position on the screen in a larger background image will draw the attention of the individual focussing his or her eyes on the small target image element for good results.

According to a further embodiment providing an eye tracker device comprises providing a head free eye tracker or a head mounted eye tracker.

Both may assure a very precise measurement of the position and the line of sight of the eyes.

According to a further embodiment the direction of gaze is one or all of the nine cardinal directions of gaze.

According to a further embodiment the direction of gaze is a straight direction of gaze.

According to a further embodiment the method is repeated while the non-dominant eye is covered by an infra-red translucent filter.

In this way it becomes possible to measure latent strabismus angles.

According to a further embodiment displaying a small image element comprises displaying the target image for a short time interval of at most 1 sec.

This assures that searching for the target element by the individual can only be accomplished by moving the direction of gaze by eye movements and not by head movements.

According to a further embodiment the method comprises storing the strabismus angle in a memory of the computer system.

By storing the angle statistical analysis of the strabismus angle becomes possible.

According to a further embodiment the method comprises measuring a resolution limit of the eyes of the individual.

The results of the method to measure the resolution limit of an eye of an individual may be used during the measurement of the strabismus angle or may be used independently. If it is used in the measurement of the strabismus angle the resolution limit of the eye may be used to determine the size of the small image elements during displaying the small image at a target position on the screen during the strabismus angle measurement. The small image may be thereby individually adapted so as to be really on the resolution limit of the individual thereby creating a very good strabismus angle measurement result.

According to a further embodiment the method comprises:

successively measuring the strabismus angle between the eyes of an individual by:

displaying successively a second, third and further small image element at a second, third and further target position on the screen;

measuring the position and line of sight of the eyes of the individual with the eye tracker device successively at the second, third and further target position;

forwarding the measured position and line of sight of the eyes from the eye tracker device to a computer system for the second, third and further target position;

calculating the strabismus angle between the eyes by calculating the difference in line of sight of the left and right eyes of the individual with the computer system successively for the second, third and further target position; and, storing the strabismus angle at the second, third and further target position in a memory of the computer system for statistical data analysis.

By storing the strabismus angle at the second, third and further target position in a memory statistical analysis of the angle becomes possible.

According to a further embodiment the method comprises displaying the strabismus angle and/or results of the statistical data analysis on the screen or another screen for a system operator.

Thereby interaction with the system operator becomes possible.

According to a further embodiment the method comprises before imaging the small image element at a target position on the screen:

measuring the position and line of sight of the eyes of the individual with the eye tracker device;

forwarding the measured position and line of sight of the eyes from the eye tracker device to a computer system;

calculating a viewing position on the screen by using the measured position and line of sight of the eyes with the computer system; and, using the computer system to display the small image element at or close to the viewing position on the screen.

This assures that the individual quickly finds the small image element.

According to a further embodiment positioning the individual with his or her eyes in front of the screen at a distance comprises positioning the individual at a viewing distance between 0 to 5 m from the screen.

Positioning the individual with his or her eyes in front of the screen at a distance may comprise positioning the individual at a viewing distance between 0.3 to 0.8 m, preferably between 0.4 to 0.6 m for a near sight test.

Positioning the individual with his or her eyes in front of the screen at a distance may comprise positioning the individual at a viewing distance between 0.8 to 5 m preferably between 1 to 3 m, preferably around 2 m for a far sight test.

In this way it becomes possible to measure the strabismus angle at near viewing distance and at far viewing distance.

The method can be used to measure strabismus angles and latent strabismus angles in all cardinal directions at near viewing distance, and for the gaze angle straight ahead for near and far viewing distances.

According to a further embodiment positioning the individual with his or her eyes in front of the screen at a distance comprises:

positioning the individual with his or her eyes in front of a near sight screen at a viewing distance between 0.3 to 0.8 m for the near sight test; and, moving the screen away to allow the individual to see a far sight screen at a viewing distance between 0.8 to 5 m, preferably between 1 to 3 m for a far sight test.

In this way it becomes possible to measure the strabismus angle at near sight and at far sight. The system may therefore have two screens, the near sight screen at a viewing distance between 0.3 to 0.8 m being moveable by a moving actuator away from the line of sight to allow the individual a view on the far sight screen at a viewing distance from 0.8 to 5 m for a far sight test.

According to a further embodiment positioning the individual with his or her eyes in front of the screen at a distance comprises:

positioning the individual with its eyes in front of a near sight screen at a viewing distance between 0.3 to 0.8 m for the near sight test; and, moving the screen away from the individual to a viewing distance between 0.8 to 5 m to allow the individual to see a far sight screen for a far sight test.

In this way it becomes possible to measure the strabismus angle at near sight and at far sight. The system may therefore have a moveable screen moveable with a moving actuator to move the screen from a viewing distance from 0.3 to 0.8 m for the near sight test to a viewing distance between 0.8 to 5 m for a far sight screen for a far sight test.

According to a further embodiment the method comprises using an infrared filter in front of the non-dominant eye of the individual.

This may be the case for the measurement of the strabismus angle in patients with latent strabismus.

It is an objective to provide an improved or alternative system, to determine a strabismus angle of the eyes of an individual.

Accordingly the system comprising:
an eye tracker device;
a screen; and
a computer system operably connected to the eye tracker device and the screen, the computer system being provided with a memory and a processor the memory being provided with computer software when run on the processor to execute the measurement method:

displaying a small image element at a target position on the screen;

measuring the position and line of sight of the eyes of the individual with the eye tracker device while the eyes are focussing at the small image element;

forwarding the measured position and line of sight of the eyes from the eye tracker device to the computer system; and, calculating the strabismus angle of the eyes by calculating the difference in line of sight between the left and right eyes of the individual with the computer system.

The eye tracker device may be a head free eye tracker such that the individual may freely move his or her head. It is advantageous that there is no need to restrain the head position and pose. Especially since most strabismus patients are toddlers, this is very important. There is also no need to attach any equipment to the patient's head.

It is an objective to provide an improved or alternative computer readable medium to determine a strabismus angle of the eyes of an individual.

Accordingly the computer readable medium is provided with computer software to determine a strabismus angle of the eyes of an individual when run on a processor of a computer connected to an eye tracker device and a screen, both positioned in front of the eyes of the individual, the computer software executing a measurement method comprising:

displaying a small image element at a target position on the screen;

measuring the position and line of sight of the eyes of the individual with the eye tracker device while the eyes are focussing at the small image element;

forwarding the measured position and line of sight of the eyes from the eye tracker device to the computer system;

calculating the strabismus angle between the eyes by calculating the difference in line of sight between the left and right eyes of the individual with the computer system

BRIEF DESCRIPTION OF THE DRAWINGS

Embodiments of the invention will be described by way of example only, with reference to the accompanying schematic drawings in which corresponding reference symbols indicate corresponding parts, and in which.

DETAILED DESCRIPTION OF THE INVENTION

Figure 1:
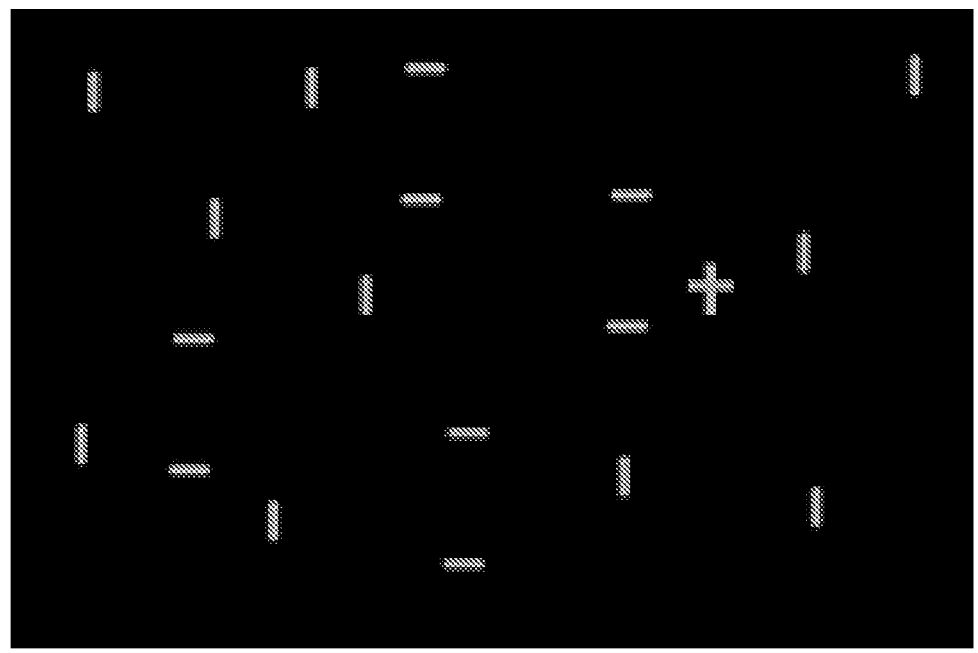
FIG. 1 schematically shows a view on the viewing screen during the measurement method.

The method to determine a strabismus angle of the eyes of an individual, comprises:

positioning the individual with his or her eyes in front of an eye tracker device and in front of a screen at a viewing distance;

having the individual focus his or her eyes on the screen;

displaying a small image element at a target position on the screen;

measuring a position and line of sight of the eyes of the individual with the eye tracker device;

forwarding the measured position and line of sight of the eyes from the eye tracker device to a computer system; and, calculating the strabismus angle of the eyes by calculating the difference in line of sight between the left and right eyes of the individual with the computer system.

By displaying a small image element at a target position on the screen the individual has to really focus his or her eyes on the screen to see the image and thereby it becomes possible to measure a position and line of sight of the eyes of the individual with the eye tracker device with high precision making a good calculation of the strabismus angle of the eyes possible.

The screen may be a cathode ray tube, a liquid crystal display (LCD), a computer monitor or display screen, a touchscreen, a projection screen, a viewing surface, or a television screen. A video projector may be used to project the images on the projection screen using a lens system.

The test may use a combination of a free head position eye tracker (placed at a fixed distance of the test subject) and a visual search stimulus presented at a monitor, seen either near sight (0.3 to 0.8 m) or at far sight (0.8 to 5 m); the test may be repeated using an infrared transmitting filter for the non-dominant eye to measure latent strabismus angle. The speed may be at least 60 frames per second.

The eye tracker may comprise two infrared sensitive cameras, measuring light and dark images of both eyes at a high speed. Both cameras may measure both eyes and both gaze directions, providing a highly accurate and precise measurement of the strabismus angles.

Eye tracker devices can be bought, for example from Tobii, for example the Tobii Eye Tracker X2-60, which has a sampling rate of 60 Hz. Information with respect to an eye tracker device for use in the invention can be gleaned, for example from U.S. Pat. No. 9,041,787 which discloses an eye tracker device which includes:

a first illuminator to selectively illuminate at least a portion of a first eye of the user;

a second illuminator to selectively illuminate at least a portion of a second eye of the user;

a first image sensor to capture image data representing images of at least a portion of the first eye of the user;

a second image sensor to capture image data representing images of at least a portion of the second eye of the user; and a control device to:

control the first illuminator and the second illuminator for the selective illumination of at least a portion of the first eye of the user and a portion of the second eye of the user;

receive the image data from the first image sensor comprising reflection of illumination from the first illuminator off a cornea of the first eye of the user;

receive the image data from the second image sensor comprising reflection of illumination from the second illuminator off a cornea of the second eye of the user;

determine a gaze target area for the user based at least in part on the position of the reflection of the illumination off the cornea of the first eye and the position of the reflection of the illumination off the cornea of the second eye. The eye tracker device may measure (large gaze) angles, up to 36 by means of video eye tracking. The device may be able to track the movements of the eyes without the use of auxiliary equipment such as a lens. Due to an algorithm, the eye tracking device may able to compensate for minor head movements thereby allowing the user to measure without restraining the head. With both these two features and a measurement accuracy of 0.5 degrees at a distance of 60 cm from cornea to the device the eye tracking device allows the user to easily perform eye tracking recordings.

Video eye tracking may be based on the pupil centre corneal reflection method to measure the position of the eyes. First, near-infrared light emitting diodes (LEDs) illuminate the eyes, causing reflections by the pupil and cornea. Then, two cameras capture these reflections. The angle of both incoming reflections creates a vector with magnitude and direction. Finally, in addition of a physiological 3D software model of the eyes, this vector is used to determine the position of the eyes in space.

Both the "bright pupil method" and the "dark pupil method to calculate the gaze position. In the bright pupil method, the reflection of the pupil is used as a point in space. While with the dark pupil method, the dark pupil is used as a reference point.

A calibration procedure comes ahead of the measurement procedure to provide the physiological 3D software model characteristics of the user's eyes. During the procedure, the user is forced to follow a stimulus that slides to nine gaze directions across a monitor. Meanwhile the eye tracking device acquires samples (60 Hz) to estimate the shape of the eye, the position of the fovea, the way of light refraction and reflection by the parts of the eyes. After the sampling, the results of the calibration procedure are depicted in nine cardinal gaze directions for both eyes. The quality of the calibration is depicted in lines. The length and direction of the line represent the distance between the calibration stimulus and the sampled gaze point. Therefore, the shortness of the line is proportional to the quality of the calibration.

We found in a group of 17 healthy non-squinting test subjects that the test works properly. The visual search stimulus comprises of a rapid succession of randomly placed small images where the subject should find one that is different.

By displaying a small image element smaller than 20 arc min, preferably smaller than 10 arc min and most preferably smaller than 2 arc min but bigger than the resolution limit of the eyes of the individual at a target position on the screen the individual has to really focus his or her eyes on the screen to see the image element and thereby it becomes possible to measure a position and line of sight of the eyes of the individual with the eye tracker device with high precision making a good calculation of the strabismus angle of the eyes possible.

Displaying a changing small image element at a target position on the screen in a larger background image will draw the attention of the individual focussing his or her eyes on the small image element for good results.

Displaying a small image element appearing at a target position on the screen in a larger background will draw the attention of the individual focussing his or her eyes on the small image element for good results.

Displaying a small target image element within a background comprises displaying the background and the target image for a short time interval—1 sec or shorter—to ensure that searching for the element by the individual can only be accomplished by moving the direction of gaze by eye movements and not by head movements.

Another major advantage is that a more natural stimulus is provided, by providing a visual search of randomly placed objects. This induces eye movements also to the cardinal gaze orientations in a more natural manner.

An infrared filter may be used in the calibration, and for the measurement of the strabismus angle in patients with latent strabismus. The eyes cannot see through the IR filter but since the eye tracker device works with IR light it can still determine the eye position behind the IR transmitting filter. For measuring latent strabismus that is important because than it becomes possible to measure the strabismus when one eye is not seeing anything because it is covered by the IR filter.

Test 1

To examine if it is possible to determine the eye positions and related strabismus angle with an eye tracker device and without having to restrain the head, a small study with healthy subjects was conducted. Measurements were done in 15 healthy (8 men and 7 women) subjects between 18 and 24 years old. Seven of the subjects were wearing glasses or contact lenses. In four lens/eyeglass wearers, there was also a cylindrical aberration. One of the subjects has a history with strabismus but has been successfully treated. The treatment consisted of eye patches and surgery.

The subjects of a first group were subjected to a stimulus test presented at a 17 inch laptop monitor with the eye tracking device placed below the screen at a distance of 50-60 cm to the eyes. During this test, subjects were asked to make a visual search for the cross (see FIG. 1), which appeared randomly but with a higher probability in one of the nine gaze directions throughout the screen every three seconds over a period of 150 seconds.

Three measurements were performed: 1) calibration with an IR filter covering the right eye, 2) calibration with an IR filter covering the left eye, and 3) without an IR filter. The total time of each measurement excluding calibration time was 150 seconds. During these measurements, each subject was asked to minimize head movements.

After the measurements of group 1, data was gathered and then assessed on the presence and distribution of gaze points in nine cardinal gaze directions.

Figure 2:
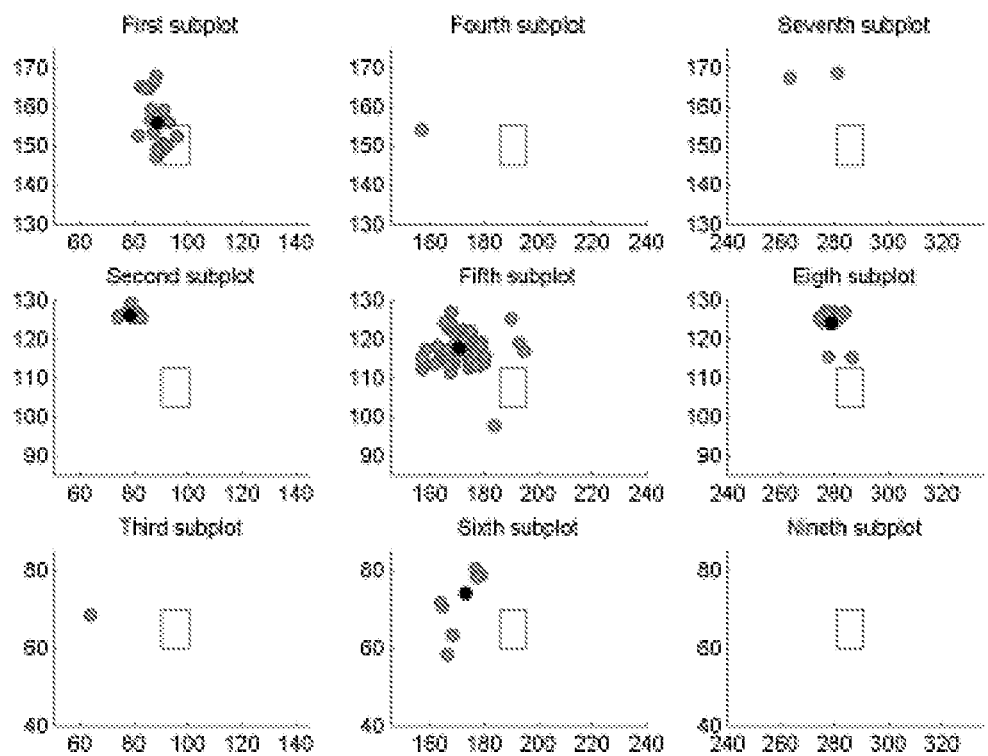
FIG. 2 schematically shows the calculated angles for all nine directions where the fixation points/position of the eyes are visible.

The calculated angles for all nine directions are saved in a document with Matlab providing a graphs (see FIG. 2) where the fixation points/position of the eyes are visible.

The squares in each subplot are the designated areas. For all the points where the left eye fixated in this area, the points of the right eye are given in the graph. The same graph is created in which the right eye fixates in the designated area and the points of the left eye are given in the graph. The results are summarized in the following table 1.

| subject | Right Eye as reference | | Left Eye as reference | |
| --- | --- | --- | --- | --- |
| | Horizontal Angle | Vertical angle | Horizontal Angle | Vertical angle |
| 1 | −0.2 | 0.1 | 0.3 | −0.1 |
| 2 | −1.4 | 0.9 | 1.7 | −0.6 |
| 3 | −1.7 | 0.8 | −0.2 | −0.4 |
| 4 | −0.2 | −0.5 | 0.8 | −0.1 |
| 5 | −1.8 | 1.0 | 1.1 | 0.0 |
| 6 | −0.5 | 0.0 | 1.9 | 0.2 |
| 7 | 1.4 | 0.1 | Failed | |
| 8 | 1.3 | −0.4 | −0.6 | −0.4 |
| 9 | 0.2 | −0.8 | −0.1 | −0.1 |
| 10 | 0.3 | 0.6 | 0.7 | −1.4 |
| 11 | −0.8 | 0.0 | 1.8 | 0.2 |
| 12 | −0.3 | 0.2 | 0.3 | −0.1 |
| 13 | −0.6 | −0.1 | 0.6 | −0.1 |
| 14 | −0.3 | 0.1 | 0.5 | 0.3 |
| 15 | −1.2 | −0.5 | 1.1 | 0.2 |

In table 1 the strabismus angles found in the participating individuals are listed. The first column depicts the subject number. Columns two and three depict the strabismus angles (left eye gaze—right eye gaze) when the right eye fixated (i.e. held gaze for 108 ms or longer) in one of nine cardinal directions for the near condition. Column two is the horizontal angle, column three is the vertical angle. Columns four and five depict the strabismus angles (right eye gaze—left eye gaze) when the left eye fixated in one of nine cardinal directions. Column four is the horizontal angle, column five the vertical angle. All angles are in degrees. Since only healthy individuals were measured in this study, expected is to find angles that are smaller than 1.5 degrees. For all subjects the strabismus angles were smaller then this criterion when the fixations of the left eye or the fixations of the right eye were taken as reference. Only for subject 7 we did not measure enough stable fixations in cardinal directions of the left eye to adequately determine the strabismus angle referring to this eye. We did not determine the dominant eye for our test subjects. Moreover since the subjects were healthy volunteers, the results for columns two and four and for columns three and five should be identical but of opposite sign. With the exception of subject three (and 7 where we only have one outcome) these values were smaller than 1 degree, suggesting that the precision of our method is approximately 1 degree.

For young individuals a 27 inch screen may be used for the calibration and visual search task. Because of the enlargement of the screen the range of the measurements will also increase. A 17 inch laptop is used by the instructor/orthoptists for the start-up. First a calibration for each eye is conducted. Calibrating each eye separately is necessary because for people with a large deviation the two eyed calibration is incorrect.

The first calibration is done with the dominant eye covered, followed with a short measurement, of 10 seconds, were the patient looks straight ahead. Then a new calibration is done with the non-dominant eye covered, and again a short measurement straight ahead. After this the options are another calibration, with both eyes or immediately starting the visual search task. Two different visual search task are made, one for adults and one for children.

In the task for adults (see FIG. 1) the patients are asked to find the cross. For visually impaired adults a second version of the same task is made in which the targets are larger.

Figure 3:
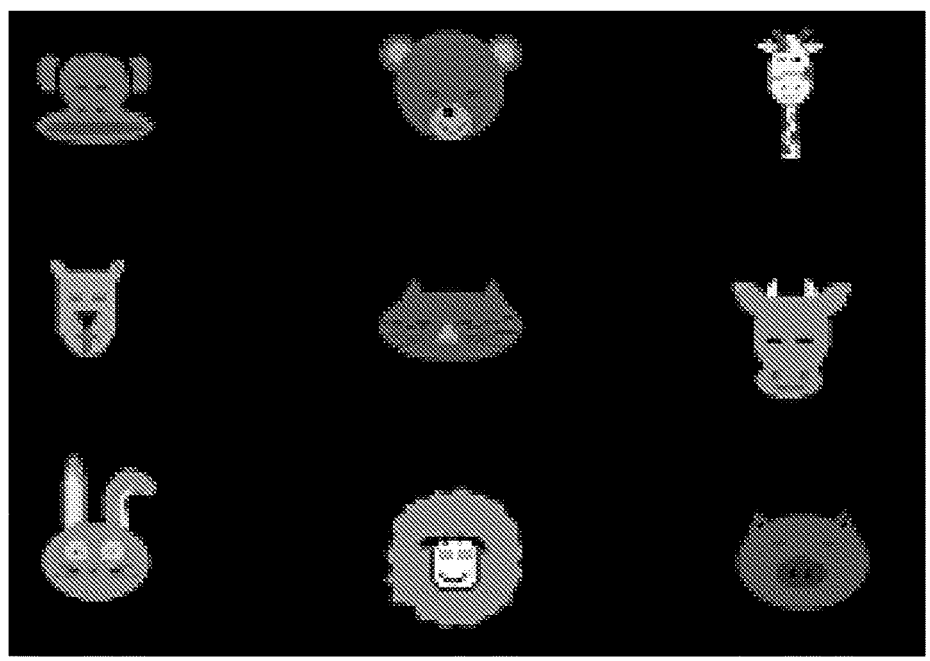
FIG. 3 schematically shows a view on the viewing screen during the measurement method for young individuals; and, FIG. 4 depicts schematically how the eye tracker can measure the horizontal and vertical gaze direction of the left and right eye of an individual making it possible to determine the strabismus angle.

In the task for young individuals there are nine animals, each in one of the cardinal points. (see FIG. 3) The children are told a story about a zoo. They are the superintendent and in the evening, the animals must go to sleep. However, sometimes there are animals, one or more, that are not sleeping. The children need to seek and identify which animals are awake. The sleeping animals have two eyes closed; the animals that are awake have one eye open. After a number of seconds changes the order of the animals and therefore the winking animals. This corresponds to the a small image element appearing or not appearing in a background image.

Test 2

In test 2, the nine cardinal directions are measured at near distance followed by straight 2.5-meter distance measurement. This test was done to examine the possibility to do the measurement of the eye positions/angle at a larger distance without having to re-calibrate when the subject looks straight ahead.

The 2.5 meter setup test was conducted on two participants (1 man and 1 woman). First, a calibration was done at a distance of 50 to 60 cm from both screen and eye-tracker. After this, the eye positions/angle at different distances were measured. Here, only the distance between the movable screen and subject was increased, while the distance between eye tracker and subject stayed the same.

The method of positioning the individual with his or her eyes in front of the screen at a distance comprises positioning the individual at various viewing distances between 0.8 to 6 m for example at 0.4, 0.6, 1.06, 1.72, 2.29, 2.79, 4.33 and 6 m for a far sight test.

In table 2 the angles (in degrees) found at the different distances (in meters) are given for both participants. In the fourth and eight row the deviation between the angle at near (60 cm for subject 1 and 45 cm for subject 2) and at the farther distance is given. Negative angles indicate that the gaze direction was downward.

| Participant 1 | | | | | | |
|---|---|---|---|---|---|---|
| Distance to screen (cm) | 60 | 106 | 172 | 229 | 279 | 433 |
| Angle (degrees) | −043 | −1.19 | −1.26 | −0.98 | −0.62 | −0.43 |
| Deviation (degrees) | 0 | −0.76 | −0.83 | −0.55 | −0.19 | 0.00 |
| Participant 2 | | | | | | |
| Distance to screen (cm) | 45 | 106 | 152 | 208 | 277 | 429 |
| Angle (degrees) | −0.31 | −1.26 | −1.10 | −1.06 | −0.77 | −0.59 |
| Deviation (degrees) | 0 | −0.95 | −0.79 | −0.75 | −0.46 | −0.27 |

The largest deviations between near and far angles were found for the smallest "far" distances (i.e. between 1 m and 2 m). We believe that this behaviour was caused by a slightly lower position of the movable screen that was used for the far measurements. This would result in a negative bias in the vertical gaze direction that would decrease for larger distances (with the inverse tangent of this position error over the distance to the screen).

For participant 1 the largest deviation found was 0.83 degrees at 172 cm, for participant 2 the largest deviation was −0.95 degrees at 106 cm.

For the largest distances errors were small, 0 degrees for participant 1 and −0.3 degrees for participant 2.

Since the difference in the angles at greater distance remain below one degree, it can be concluded that it is not necessary to recalibrate for the measurement at 2.5 meters or 4.5 meters for measuring straight ahead gaze. However, it is important that the centre position of the screen/target are the same for the measurements at 0.6 meter and 2.5 meter. So that no movements of the eyes are caused by such a misalignment. To ensure that such a misalignment causes gaze angle changes smaller than 0.3 degrees the centres of the screens should not change more than 1.3 cm.

Strabismus Angles Calculation

Figure 4:
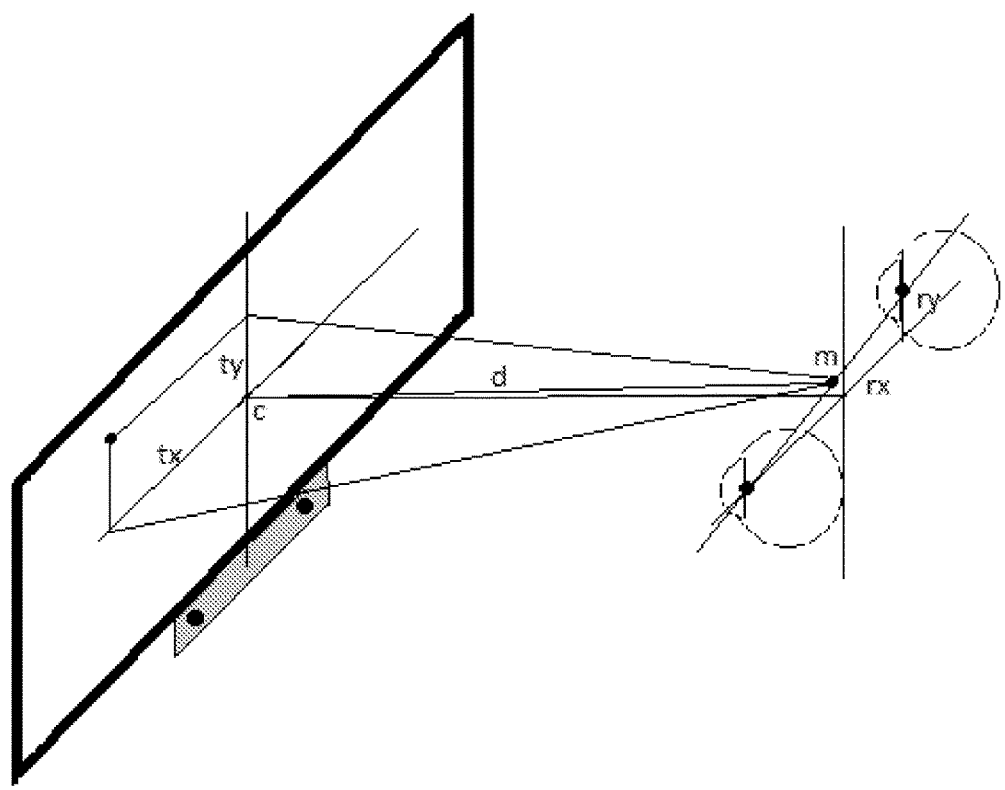

FIG. 4 depicts schematically how the eye tracker can determine the horizontal and vertical gaze direction of the left and right eye of an individual making it possible to determine the strabismus angle. The eye tracker records therefore 60× per second the distance between the center of the eye tracker and the midpoint (m) between the position of the two eye pupils. Since the position of the tracker with respect to the monitor screen is known we can infer the distance between the middle of the screen (c) and the midpoint (m), this is the head distance (d). We also know for each recorded and calibrated eye the position of the pupil (in the figure (rx) and (ry)) and the gaze position on the screen (tx, ty). The horizontal gaze direction then is given by the angle atan 2(tx,d); the vertical gaze direction by the angle atan 2(ty,d). The strabismus angle is determined by the difference between the horizontal and vertical gaze direction for the left and right eye.

These angles can be corrected for the head position error due to head movements by the angles atan 2(m−c',d) and atan 2(rx−lx,d). Note that this correction does not change the measured strabismus angle, but instead corrects for the gaze direction. These angles can also be corrected for head tilt effects through the estimates atan 2(2*ry, rx−lx) for the right eye and atan 2(2*ly, rx−lx) for the left eye.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

It will be apparent to those skilled in the art that various modifications can be made to the device and method without departing from the scope as defined in the claims.

The invention claimed is:

1. A method to determine a strabismus angle between the eyes in a direction of gaze of an individual comprising:
    providing an eye tracker device to follow the viewing direction of the eyes of the individual;
    positioning the individual in front of a screen at a viewing distance;
    having the individual to view on the screen;
    measuring a position and line of sight of the eyes of the individual with the eye tracker device; and
    forwarding the measured position and line of sight of the eyes from the eye tracker device to a computer system;
    wherein the method comprises:
    displaying a small image element at a target position on the screen to have the individual to focus his or her eyes on the small image element on the screen; and
    calculating the strabismus angles between the eyes by calculating the difference in the horizontal and vertical gaze directions between the eyes of the individual with a computer system when a dominant eye gazes in the direction of the small image element.

2. The method according to claim 1, wherein displaying a small image element comprises displaying an image element smaller than 20 arc min, preferably smaller than 10 arc min and most preferably smaller than 2 arc min but at least at the resolution limit of the eyes of the individual.

3. The method according to claim 1, wherein the method further comprises:
    using the computer system to display the small image element at the target position on the screen;
    calculating a viewing position on the screen by using the measured position and line of sight of the eyes with the computer system;
    calculating a distance between the target position on the screen and the calculated viewing position of the dominant eye on the screen;
    if the distance is smaller than 60 arc min calculating the strabismus angle between the eyes by calculating the difference in line of sight of the left and right eyes of the individual with the computer system.

4. The method according to claim 1, wherein displaying a small image element at a position on the screen comprises displaying the small image element at a position on the screen within a background image and measuring the position and line of sight of the eyes of the individual with the eye tracker device while the individual scans the background to find the small image element.

5. The method according to claim 1, wherein displaying a small image element at a position on the screen comprises displaying a small image element appearing or not appearing at a position on the screen within a background image and measuring the position and line of sight of the eyes of the individual with the eye tracker device while the individual scans the background to find the small image element.

6. The method according to claim 1, wherein providing an eye tracker device comprises providing a head free eye tracker or a head mounted eye tracker.

7. The method according to claim 1, wherein the direction of gaze is one or all of the nine cardinal directions of gaze.

8. The method according to claim 1, wherein the direction of gaze is a straight direction of gaze.

9. The method according to claim 1, wherein the above method is repeated while the non-dominant eye is covered by an infra-red translucent filter.

10. The method according to claim 1, wherein displaying a small image element comprises displaying the target image for a short time interval of at most 1 sec.

11. The method according to claim 1, wherein the method comprises storing the strabismus angle in a non-transitory memory of the computer system.

12. The method according to claim 1, wherein the method comprises measuring a resolution limit of the eyes of the individual.

13. The method according to claim 1, wherein the method comprises:
   successively measuring the strabismus angle of the eyes of an individual by:
   displaying successively a second, third and further small image element at a second, third and further target position on the screen;
   measuring the position and line of sight of the eyes of the individual with the eye tracker device successively at the second, third and further target position;
   forwarding the measured position and line of sight of the eyes from the eye tracker device to a computer system for the second, third and further target position;
   calculating the strabismus angle of the eyes by calculating the difference in line of sight of the left and right eyes of the individual with the computer system successively for the second, third and further target position; and,
   storing the strabismus angle at the second, third and further target position in a non-transitory memory of the computer system for statistical data analysis.

14. The method according to claim 1, further comprising displaying the strabismus angle and/or results of the statistical data analysis on the screen or another screen for a system operator.

15. The method according to claim 1, wherein before imaging the small image element at a target position on the screen the method comprises:
   measuring the position and line of sight of the eyes of the individual with the eye tracker device;
   forwarding the measured position and line of sight of the eyes from the eye tracker device to a computer system;
   calculating a viewing position on the screen by using the measured position and line of sight of the eyes with the computer system; and,
   using the computer system to display the small image element at or close to the viewing position on the screen.

16. The method according to claim 1, wherein positioning the individual with his or her eyes in front of the screen at a distance comprises positioning the individual at a viewing distance between 0 to 5 m from the screen.

17. The method according to claim 1, wherein positioning the individual with his or her eyes in front of the screen at a distance comprises positioning the individual at a viewing distance between 0.3 to 0.8 m, preferably 0.4 to 0.6 m for a near sight test.

18. The method according to claim 1, wherein positioning the individual with his or her eyes in front of the screen at a distance comprises positioning the individual at a viewing distance between 0.8 to 5 m preferably between 1 to 3 m, preferably around 2 m for a far sight test.

19. The method according to claim 1, wherein positioning the individual with his or her eyes in front of the screen at a distance comprises:
   positioning the individual with his or her eyes in front of a near sight screen at a viewing distance between 0.3 to 0.8 m for the near sight test; and,
   moving the screen away to allow the individual to see a far sight screen at a viewing distance between 0.8 to 5 m, preferably between 1 to 3 m for a far sight test.

20. The method according to claim 1, wherein positioning the individual with his or her eyes in front of the screen at a distance comprises:
   positioning the individual with his or her eyes in front of a near sight screen at a viewing distance between 0.3 to 0.8 m for the near sight test; and,
   moving the screen away from the individual to a viewing distance between 0.8 to 5 m, and enlarging the screen such that it extends 30 degrees horizontally by 25 degrees vertically, and repeating the calibration procedure, to allow the individual to see a far sight screen for a far sight test in all nine cardinal gaze directions.

21. The method according to claim 1, wherein the method comprises using an infrared filter in front of the non-dominant eye of the individual to test for latent strabismus.

22. A system to determine a strabismus angle of the eyes of an individual, comprising:
   an eye tracker device;
   a screen; and
   a computer system operably connected to the eye tracker device and the screen, the computer system being provided with a non-transitory memory and a processor the memory being provided with computer software when run on the processor to execute a measurement method according to claim 1.

23. The system according to claim 22, wherein the eye tracker device is a head free eye tracker or a head mounted eye tracker.

24. A non-transitory computer readable medium provided with computer software to determine a strabismus angle of the eyes of an individual when run on a processor of a computer connected to an eye tracker device and a screen, both positioned in front of the eyes of the individual, the computer software executing a measurement method according to claim 1.

25. A non-transitory computer readable medium provided with computer software to determine a strabismus angle of the eyes of an individual when run on a processor of a computer connected to an eye tracker device and a screen, both positioned in front of the eyes of the individual, the software executing the following steps:
   displaying a small image element at a target position on the screen;

measuring the position and line of sight of the eyes of the individual with the eye tracker while the eyes are focusing at the small image element;

forwarding the measured position and line of sight of the eyes from the eye tracker device to the computer system; and calculating the strabismus angle between the eyes by calculating the difference in line of sight of the left and right eyes of the individual with the computer system.

\* \* \* \* \*